United States Patent [19]

Hadley et al.

[11] Patent Number: 5,688,790
[45] Date of Patent: Nov. 18, 1997

[54] PHENYLPYRROLE DERIVATIVES AND THEIR USE AS ANTIPSYCHOTIC AGENTS

[75] Inventors: Michael Stewart Hadley, Sawbridgeworth; Christopher Norbert Johnson, Saffron Walden; Geoffrey Stemp, Bishop's Stortford, all of England

[73] Assignee: SmithKline Beecham Plc, Brentford, England

[21] Appl. No.: 532,548

[22] PCT Filed: Mar. 29, 1994

[86] PCT No.: PCT/EP94/00992

§ 371 Date: Sep. 28, 1995

§ 102(e) Date: Sep. 28, 1995

[87] PCT Pub. No.: WO94/24129

PCT Pub. Date: Oct. 27, 1994

[30] Foreign Application Priority Data

Apr. 8, 1993 [GB] United Kingdom ............. 9307400

[51] Int. Cl.$^6$ .................. C07D 471/04; C07D 455/02; A61K 31/435
[52] U.S. Cl. .................. 514/214; 514/299; 514/306; 514/413; 540/593; 546/112; 546/138; 548/453
[58] Field of Search ............... 514/214, 299, 514/306, 413; 540/593; 546/112, 138; 548/453

[56] References Cited

U.S. PATENT DOCUMENTS

| | | | |
|---|---|---|---|
| 5,330,990 | 7/1994 | Hansen | 514/299 |
| 5,523,299 | 6/1996 | Stemp et al. | 514/183 |

FOREIGN PATENT DOCUMENTS

| | | |
|---|---|---|
| 0036269 | 9/1981 | European Pat. Off. |
| 0241053 | 10/1987 | European Pat. Off. |
| 0259930 | 3/1988 | European Pat. Off. |

OTHER PUBLICATIONS

J Med Chem vol. 35, No. 13, 1992, pp. 2355–2363; I. Peterson et al; 'Conformational analysis of dopamine D–2 receptor antagonists of the benzamide series in relation to a recently proposed D–2 receptor-interaction model'.

Primary Examiner—Mukund J. Shah
Assistant Examiner—Deepak R. Rao
Attorney, Agent, or Firm—Nora Stein-Fernandez; Janice E. Williams; Edward T Lentz

[57] ABSTRACT

This invention relates to compounds of formula (I):

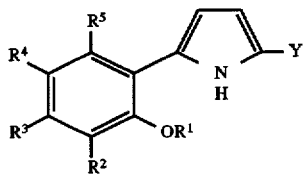

Formula (I)

wherein
$R^1$ represents $C_{1-4}$alkyl; and
$R^2$, $R^3$, $R^4$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxyl, hydroxy$C_{1-4}$alkyl, $C_{1-4}$alkylthio, $C_{1-4}$alkanoyl, $C_{1-4}$alkoxycarbonyl, aminosulphonyl, or mono- or di$C_{1-4}$alkylaminosulphonyl; or
$R^1$ and $R^2$ together form a linking chain $-(CH_2)_mOp$; (wherein m is 2 to 4 and p is zero or 1) which chain may be optionally substituted by one or two $C_{1-4}$alkyl groups; and Y represents a group of formula ($\alpha$):

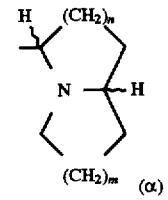

(α)

wherein each of n and m independently represent an integer from 1 to 3;
and salts thereof, having activity at dopamine receptors and potential utility in the treatment of psychoses such as schizophrenia.

7 Claims, No Drawings

PHENYLPYRROLE DERIVATIVES AND THEIR USE AS ANTIPSYCHOTIC AGENTS

This application is a 371 of PCT/EP94/00992 filed on Mar. 29, 1994.

The present invention relates to novel phenylpyrrole derivatives, processes for their preparation, pharmaceutical compositions containing them and their use in therapy, in particular as and psychotic agents.

European Patent Application No. 241053, describes compounds of the formula:

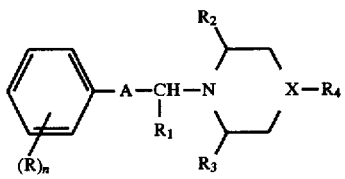

wherein A is an unsaturated 5-membered heterocyclic ring, such as 2,5-pyrrolyl, or 3,5- or 1,4- pyrazolyl; X is a nitrogen or carbon atom; $R_1$, $R_2$, $R_3$ are each hydrogen or alkyl; $R_4$ is aryl, heteroaryl, arylcarbonyl or heteroaryl-carbonyl; R is selected from a variety of substituents and n is 0–4. The compounds are said to have antipsychotic properties.

European Patent Application No. 259930 describes compounds of the formula:

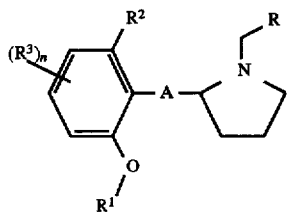

wherein A is an unsaturated 5-membered heterocyclic ring, such as 2,5-pyrrolyl, 1,4-pyrazolyl or 2,5-furyl; R is hydrogen, alkyl or optionally substituted phenyl; $R^1$ is alkyl, alkenyl or forms a ring with the phenyl group; $R^2$ is hydrogen, hydroxy or alkoxy; $R^3$ is selected from a variety of substituents and n is 0–3. These compounds are also said to have antipsychotic properties.

We have now found a novel class of 2-phenylpyrroles which exhibit dopamine antagonist activity and thus have potential as antipsychotic agents.

In a first aspect the present invention provides compounds of formula (I):

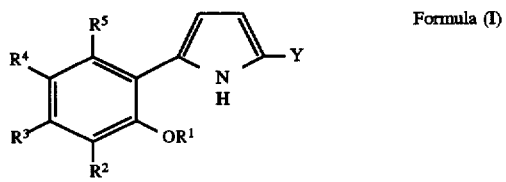

Formula (I)

wherein
$R^1$ represents $C_{1-4}$alkyl; and
$R^2$, $R^3$, $R^4$ and $R^5$ each independently represent hydrogen, halogen, $C_{1-4}$alkyl, $C_{1-4}$alkoxy, $C_{1-4}$alkoxyC$_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxyl, hydroxyC$_{1-4}$alkyl, $C_{1-4}$alkylthio, $C_{1-4}$alkanoyl, $C_{1-4}$alkoxycarbonyl, aminosulphonyl, or mono- or diC$_{1-4}$alkylaminosulphonyl; or $R^1$ and $R^2$ together form a linking chain —(CH$_2$)$_m$Op; (wherein m is 2 to 4 and p is zero or 1) which chain may be optionally substituted by one or two $C_{1-4}$alkyl groups; and Y represents a group of formula:

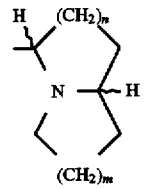

wherein each of n and m independently represent an integer from 1 to 3; and salts thereof.

In the compounds of formula (I) an alkyl group or moiety may be straight or branched. Alkyl groups which may be employed include methyl, ethyl, n-propyl, n-butyl, n-pentyl; n-hexyl and any branched isomers thereof such as isopropyl, t-butyl, sec-pentyl and the like.

A halogen atom present in the compounds of formula (I) may be a fluorine, chlorine, bromine or iodine atom.

When $R^1$ and $R^2$ together form a group —(CH$_2$)$_m$Op wherein p is 1 it will be appreciated that the oxygen atom is attached to the phenyl ring at the $R^2$ position:

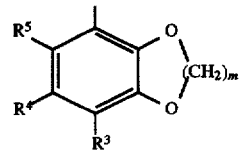

When the (CH$_2$)$_m$ moiety is substituted by two $C_{1-4}$alkyl groups these are preferably substituted on the same carbon atom e.g. a gem-dimethyl substituent.

Representative aryl groups or moieties present in any of the substituents $R^2$, $R^3$, $R^4$ and $R^5$ in compounds of formula (I) include phenyl, naphthyl, and tetrahydronaphthyl. Suitable examples of heteroaryl groups include both 5 and 6-membered heterocycles containing one or more oxygen, sulphur or nitrogen atoms, such as furyl, thienyl, pyrryl, oxazolyl, thiazolyl, imidazolyl, oxadiazolyl, thiadiazolyl, pyridyl, pyridazyl, pyrimidyl and pyrazyl. Suitable substituents for said aryl and heteroaryl groups include halogen, $C_{1-4}$alkyl, $C_{1-4}$alkoxy, $C_{1-4}$alkoxyC$_{1-4}$alkyl, nitro, cyano, amino, mono- or diC$_{1-4}$alkylamino, trifluoromethyl, trifluoromethoxy, hydroxy, hydroxyC$_{1-4}$alkyl, $C_{1-4}$alkanoyl and $C_{1-4}$alkoxycarbonyl.

$R^1$ preferably represents methyl or ethyl, or together with $R^2$ forms a $C_{2-3}$alkylene chain.

Preferably at least one of $R^2$ to $R^5$ is hydrogen, and the other substituents are selected from halogen, $C_{1-2}$alkyl, $C_{1-2}$alkoxy, phenylsulphonyl, $C_{1-3}$alkylsulphonyl, $CF_3$ and $CF_3O$.

In the group Y n is preferably 1 or 2 and m is preferably 1 or 2. For example n may be 1 and may be 2 or n and m may both be 1 or n and m may both be 2.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, acetic, benzoic, p-toluenesulphonic, methanesulphonic or naphthalenesulphonic acid. Other non-physiologically acceptable salts may be used, for example in the isolation of compounds of formula (I) and are included within the scope of this invention. Also included within the scope of the invention are solvates and hydrates of compounds of formula (I).

The compounds of formula (I) contain two asymmetric centres and therefore exist in the form of diastereoisomers. All possible diastereomeric forms (individual diastereoisomers and mixtures thereof) of compounds of formula (I) are included within the scope of the invention. The diastereoisomers of compounds of formula (I) include pairs of enantiomers. The present invention includes within its scope all such enantiomers and mixtures, including racemates.

In particular compounds (I) can exist as pairs of syn and anti diastereoisomers with regard to the relative orientation of the hydrogen atoms shown in the group Y below:

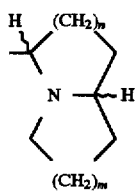

Preferred compounds of the present invention are those compounds of formula (I) contained in the slower eluting pair of diastereoisomers (the antidiastereoisomers) from neutral alumina chromatography.

Particular compounds according to the invention include:
2-[9-(6,9-anti-(1-azabicyclo[4.3.0]nonyl))]-5-(3,5-dibromo-2-methoxyphenyl)-1H-pyrrole,
2-[2-(2,6-anti-(1-azabicyclo[4.4.0]decyl))]-5-(3,5-dibromo-2-methoxyphenyl)-1H-pyrrole,
2-[9-(6,9-anti-(1-azabicyclo[4.3.0]nonyl))]-5-(5-ethylsulphonyl-2-methoxyphenyl)-1H-pyrrole,
2-[2-(2,6-anti-(1-azabicyclo[4.4.0]decyl))]-5-(3-bromo-5-ethylsulphonyl-2-methoxyphenyl)-1H-pyrrole,
2-[9-(6,9-anti-(1-azabicyclo[4.3.0]nonyl))]-5-(3-bromo-5-ethylsulphonyl-2-methoxyphenyl)-1H-pyrrole,
2-[9-(6,9-syn-(1-azabicyclo[4.3.0]nonyl))]-5-(3,5-dibromo-2-methoxyphenyl)-1H-pyrrole,
2-[2-(2,6-syn-(1-azabicyclo[4.4.0]decyl))]-5-(3,5-dibromo-2-methoxyphenyl)-1H-pyrrole,
2-[9-(6,9-syn-(1-azabicyclo[4.3.0]nonyl))]-5-(5-ethylsulphonyl-2-methoxyphenyl)-1H-pyrrole,
2-[2-(2,6-syn-(1-azabicyclo[4.4.0]decyl))]-5-(3-bromo-5-ethylsulphonyl-2-methoxyphenyl)-1H-pyrrole,
2-[9-(6,9-syn-(1-azabicyclo[4.3.0]nonyl))]-5-(3-bromo-5-ethylsulphonyl-2-methoxyphenyl)-1H-pyrrole,
and salts thereof.

The present invention also provides a process for preparing compounds of formula (I) which process comprises:
carrying out a Vilsmeier reaction with a compound of formula (II):

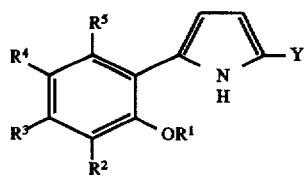

Formula II and an oxo derivative of the group Y:

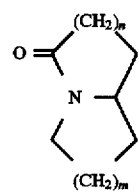

Formula III and reducing the intermediate product with, for example, sodium borohydride or sodium cyanoborohydride;
and optionally thereafter forming a salt of formula (I).

The Vilsmeier reaction may be effected according to conventional methods. Thus, for example, the oxo derivative of the group Y may first be reacted with phosphorus oxychloride ($POCl_3$) and the resulting product subsequently reacted with a compound of formula (II) conveniently in a solvent such as dichloromethane. The product of this reaction is then reduced with, for example, sodium borohydride or cyanoborohydride. The reduction may be carried out in a suitable solvent, for example dichloroethane dichloromethane, methanol, ethanol, water or mixtures thereof.

A compound of formula (II) may be prepared by cyclisation of a dicarbonyl compound of formula (IV):

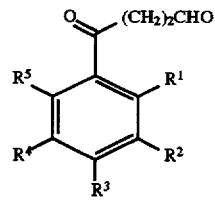

Formula IV

The reaction may be effected using an ammonium salt, e.g. ammonium acetate, in a solvent such as ethanol. (See, for example, C. G. Kruse et al., Heterocycles, vol 26, P3141, 1987).

A compound of formula (IV) may itself be prepared by reacting the appropriate substituted benzoyl halide with a metallo derivative of a 2-(2-haloethyl)-1,3-dioxolane or 2-(2-haloethyl)-1,3-dioxane and subsequent acid hydrolysis.

Compounds of formula (III) which may be employed in the above process include 3-indolizidinone and 4-quinolizidinone. Such compounds may be prepared by methods described in the literature (e.g. Chem. Abs., 1964, 60, 1691f and Chem. Abs., 1963, 59, 3889d).

When a compound of formula (I) is obtained as a mixture of enantiomers these may be separated by conventional methods such as crystallisation in the presence of a resolving agent, or chromatography, for example using a chiral HPLC column.

Compounds of formula (I) have been found to exhibit affinity for dopamine receptors, in particular $D_3$ receptors, and are expected to be useful in the treatment of disease states which require modulation of such receptors, such as psychotic conditions. The therapeutic effect of currently available antipsychotic agents (neuroleptics) is generally believed to be exceed via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors. In particular compounds of formula (I) are dopamine $D_3$ receptor antagonists and as such are of potential use as antipsychotic agents for example in the treatment of schizophrenia, schizo-affective disorders, psychotic depression and mania. Other conditions which may be treated by modulation of dopamine $D_3$ receptors include dyskinetic disorders such as Parkinson's disease, neuroleptic-induced parkinsonism and tardive dyskinesias; depression; and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg. e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The invention is further illustrated by the following non-limiting examples:

EXAMPLE 1

2-[9-(1-Azabicyclo[4.3.0]nonyl)]-5-(3,5-dibromo-2-methoxyphenyl)-1H-pyrrole hydrochloride (6,9-syn- and 6,9-anti- isomers)

Phosphorus oxychloride (0.25 ml, 2.7 mmol) was added to 3-indolizidinone (0.34 g, 2.4 mmol) [Chem. Abstr., 1964, 60, 1691f] at room temperature under argon with constant stirring. The resulting viscous oil was stirred at 40° C. for 16 hours and then 1,2-dichloroethane (2 ml) was added. The reaction mixture was cooled to 0° C., then a solution of 2-(3,5-dibromo-2-methoxyphenyl)-1H-pyrrole (0.405 g, 1.2 mmol) in 1,2-dichloroethane (4 ml) was added dropwise. The reaction mixture was stirred at 0° to 5° C. for 2 hours, then at room temperature for 18 hours. Sodium borohydride (0.418 g, 11.1 mmol) was added portionwise with ice cooling and stirring at room temperature was carried out for 3 hours. The mixture was cooled to 0° C. and treated dropwise with water (2 ml) followed by methanol (2 ml). When effervescence had subsided, the mixture was poured onto water (30 ml) and extracted with dichloromethane (3×30 ml). The combined organic extracts were dried over anhydrous sodium sulphate, then evaporated in vacuo to give an oil. The borane complex was treated With a mixture of hydrochloric acid (35%; 2.0 ml) and methanol (4.0 ml) and the resulting solution stirred for 18 hours. The solution was treated with water (20 ml) and aqueous sodium hydroxide (40%; 2.55 ml) then extracted with dichloromethane (3×30 ml). The combined extracts were dried over anhydrous sodium sulphate and evaporated in vacuo to give an oil (0.70 g). Chromatography on alumina (Brockmann grade 1) with ether (30–100%)—pentane gradient elution followed by ether-methanol (0–1%) gradient elution gave the free base of the title compound as two pairs of diastereoisomers. Faster eluting pair A (0.135 g) and slower eluting pair B (0.186 g) were isolated as colourless oils. Faster eluting pair A (0.122 g) was dissolved in ether, and the solution washed with water (3×20 ml), then extracted with hydrochloric acid (0.1M; 3×30 ml). The combined aqueous extracts were extracted with dichloromethane (3×30 ml), and the combined organic extracts were dried over anhydrous sodium sulphate and evaporated in vacuo to give the title compound (faster eluting pair of diastereoisomers A) as a white foam (0.129 g, 22%). The hydrochloride salt of the slower eluting pair of diastereoisomers B (0.114 g; 19%) was prepared in an analogous manner from the free base (0.175 g), and obtained as a white foam.

Faster Eluting Pair of Diastereoisomers A -Syn (Free Base)

NMR δ (200 MHz; CDCl$_3$) 1.18–1.32 (2H,m), 1.40–1.69 (4H,br m), 1.73–1.93 (4H, br m), 1.95–2.15 (2H,br m), 2.81–2.94 (1H,br m), 3.25–3.40 (1H, br m), 3.73 (3H, s), 6.09 (1H,br s), 6.48 (1H,br s), 7.46 (1H,d), 7.63 (1H,br s) and 9.71 (1H,br s).

Slower Eluting Pair of Diastereoisomers B -Anti (Free Base)

NMR δ (200 MHz; CDCl$_3$) 1.15–1.36 (2H,m), 1.40–1.63 (3H,m), 1.66–1.95 (3H,m), 2.02–2.21 (2H,m), 2.28–2.47 (1H,m), 2.61–2.78 (1H,m), 2.82–2.92 (1H,m), 3.73 (3H,s), 4.26–4.34 (1H,m), 6.06 (1H,t), 6.52 (1H,t), 7.47 (1H,d), 7.63 (1H,d) and 9.62 (1H,br s).

EXAMPLE 2

2-[2-(1-Azabicyclo[4.4.0]decyl)]-5-(3,5-dibromo-2-methoxyphenyl)-1H-pyrrole hydrochloride (2,6-syn- and 2,6-anti- isomers)

Phosphorus oxychloride (0.17 ml, 1.82 mmol) was added to 4-quinolizidinone (0.28 g, 1.83 mmol) [Chem. Abstr., 1963, 59, 3889d] at room temperature under argon with constant stirring. The resulting viscous oil was stirred at 40° C. for 2 hours and then 1,2-dichloroethane (1.4 ml) was added. The reaction mixture was cooled to 0° C., then a solution of 2-(3,5-dibromo-2-methoxyphenyl)-1H-pyrrole (0.406 g, 1.23 mmol) in 1,2-dichloroethane (4 ml) was added dropwise. The reaction mixture was allowed to warm to room temperature and was stirred for 18 hours at 20° C. and then for 3 hours at 70°–80° C. Sodium borohydride (0.423 g, 11.0 mmol) was added portionwise with ice cooling, and stirring at room temperature was carried out for 3 hours. The mixture was cooled to 0° C. and treated dropwise with water (2 ml) followed by methanol (2 ml). When effervescence had subsided, the mixture was poured onto water (30 ml) and extracted with dichloromethane (3×30 ml). The combined organic extracts were dried over anhydrous sodium sulphate, then evaporated in vacuo to give an oil. The borane complex was treated with a mixture of hydrochloric acid (35%; 2 ml) and methanol (4 ml) and the resulting solution stirred for 18 hours at room temperature. The solution was treated with water (20 ml) and aqueous sodium hydroxide (40%; 2.6 ml) then extracted with dichloromethane (3×30 ml). The combined extracts were dried over anhydrous sodium sulphate and evaporated in vacuo to give an oil (0.70 g). Chromatography on alumina (Brockmann grade 1) with ethyl acetate (10–100%)—pentane gradient elution followed by ethyl acetate—methanol (0–1%) gradient elution gave the free base of the title compound as two pairs of diastereoisomers. Faster eluting pair A (0.378 g) and slower eluting pair B (0.063 g) were isolated as yellow oils. Faster eluting pair A (0.43 g) was dissolved in diethyl ether, and the solution was washed with water (3×20 ml), then extracted with hydrochloric acid (0.1M; 3×30 ml). The combined aqueous extracts were extracted with dichloromethane (3×30 ml), and the combined organic extracts were dried over anhydrous sodium sulphate and evaporated in vacuo to give the title compound (faster eluting pair of diastereoisomers A) as a white foam (0.37 g, 60%). The hydrochloride salt of the slower eluting pair of diastereoisomers B was prepared in an analogous manner from the free base (0.063 g) and was obtained as a white foam (0.036 g, 6%).

Faster Eluting Pair Of Diastereoisomers A -Syn (Hydrochloride Salt)

NMR δ (400 MHz; CDCl$_3$) 1.40–1.52 (1H,m), 1.60–1.81 (2H,m), 1.81–1.96 (3H,m), 1.99–2.23 (4H,m), 2.28–2.43 (2H,m), 2.80–2.93 (2H,m), 3.22–3.30 (1H,m), 3.80 (3H,s), 3.76–3.85 (1H,m), 6.20 (1H,t), 6.66 (1H,t), 7.51 (1H,d), 7.94 (1H,d), 11.57 (1H,br s) and 11.94 (1H,br s).

Slower Eluting Pair Of Diastereoisomers B -Anti (Hydrochloride Salt)

NMR δ (400 MHz; CDCl$_3$) 1.51–1.95 (6H,m), 1.96–2.39 (4H,m), 2.61–2.84 (2H,m), 2.85–2.89 (1H,m), 3.00–3.19 (1H,m), 3.64–3.75 (1H,m), 3.78 (3H,s), 4.42–4.53 and 5.09–5.18 (1H, 2x m), 6.24, 6.45, 6.66 and 6.71 (2H,4x br s), 7.52 (1H,br s), 7.90 (1H,br s), 10.83 and 12.30 (1H, 2x br s) and 11.39 (1H,br s).

EXAMPLE 3

2-[9-(1-Azabicyclo[4.3.0]nonyl)]-5-(5-ethylsulphonyl-2-methoxyphenyl)-1H-pyrrole hydrochloride (6,9-syn- and 6,9-anti- isomers)

The title compound was prepared by a method analogous to that used to prepare example 1, but using 2-(5-ethylsulphonyl-2-methoxyphenyl)-1H-pyrrole in place of 2-(3,5-dibromo-2-methoxyphenyl)-1H-pyrrole.

Faster fluting pair of diastereoisomers A -Syn (hydrochloride salt)

NMR δ (CDCl$_3$) 1.28 (3H, t, J=7 Hz), 1.45 (1H, m), 1.76 (2H, m), 2.04 (2H, m), 2.22 (2H, m), 2.43 (3H, m), 2.69 (1H, m), 2.95 (1H, m), 3.20 (2H, q, J=7 Hz), 3.42 (1H), m), 3.98 (1H, q, J=10 Hz), 4.15 and 4.22 (3H, 2x s), 6.28 and 6.32 (1H, 2x t, J=3 Hz), 6.60 and 6.64 (1H, 2x t, J=3 Hz), 7.07 and 7.09 (1H, 2x d, J=9 Hz), 7.7 (1H, dd, J=9 Hz and 2 Hz), 8.12 and 8.15 (1H, 2x d, J=2 Hz), 11.34 and 11.70 (1H, 2x br.s) and 12.00 and 12.23 (1H, 2x br.s).

Mass spectrum: Found M$^+$ 388.1826; C$_{21}$H$_{28}$N$_2$O$_3$S requires 388.1821

Slower fluting pair of diastereoisomers B -Anti (hydrochloride salt)

NMR δ (CDCl$_3$) 1.28 (3H, t, J=7 Hz), 1.30–2.50 (8H, m), 2.69 (2H, m), 3.09 (1H, m), 3.17 (2H, q, J=7 Hz), 3.45 (1H, m), 3.90 (1H, br.s), 4.17 (3H,m), 4.57 and 5.35 (1H, 2x br.s), 6.31 (1H, t, J=3 Hz), 6.62 and 6.72 (1H, 2x m), 7.09 (1H, d, J=9 Hz), 7.72 (1H, d, J=9 Hz), 8.14 (1H, s), 10.58 and 12.42 (1H, 2x br.s) and 11.40 (1H, br.s).

Mass spectrum: Found M$^+$ 388.1827; C$_{21}$H$_{28}$N$_2$O$_3$S requires 388.1821

EXAMPLE 4

2-[2-(1-Azabicyclo[4.4.0]decyl)]-5-(3-bromo-5-ethylsulphonyl-2-methoxyphenyl)-1H-pyrrole hydrochloride (2,6-syn- and 2,6-anti- isomers)

The title compound was prepared by a method analogous to that used to prepare example 2, but using 2-(3-bromo-5-ethylsulphonyl-2-methoxyphenyl)-1H-pyrrole in place of 2-(3,5-dibromo-2-methoxyphenyl)-1H-pyrrole. It was necessary, however, to perform the Vilsmeier reaction at 100° C. instead of at room temperature, in order to effect total conversion to the desired products.

Faster eluting pair of diastereoisomers A -Syn (hydrochloride salt)

NMR δ (CDCl$_3$) 1.35 (3H, t, J=7 Hz), 1.46 (1H, m), 1.72 (3H, m), 1.90 (2H, m), 2.08 (4H, m), 2.35 (2H, m), 2.85 (2H, m), 3.26 (1H, d), 3.41 (2H, q, J=7 Hz), 3.81 (1H, m), 3.86 (3H, s), 6.22 (1H, t, J=3 Hz), 6.70 (1H, t, J=3 Hz), 7.96 (1H, d, J=2 Hz), 8.26 (1H, d, J=2 Hz), 11.62 (1H, br.s) and 11.88 (1H, br.s).

Mass spectrum: Found M$^+$ 480.1055; C$_{22}$H$_{29}$BrN$_2$O$_3$S requires 480.1082

Slower eluting pair of diastereoisomers B -Anti (hydrochloride salt)

NMR δ (CDCl$_3$) 1.34 (3H, t, J=7 Hz), 1.62 (7H, m), 1.88 (1H, m), 2.00 (1H, m), 2.12 (1H, m), 2.70 (2H, m), 2.94 (1H, m), 3.05 (1H, m), 3.37 (2H, q, J=7 Hz), 3.70 (1H, m), 3.86 (3H, s), 4.50 (1H, m), 6.26 (1H, br.s), 6.70 (1H, br.s), 7.96 (1H, d, J=2 Hz), 8.22 (1H, d, J=2 Hz), 11.69 (1H, br.s) and 12.09 (1H, br.s).

Mass spectrum: Found M$^+$ 480.1087; C$_{22}$H$_{29}$BrN$_2$O$_3$S requires 480.1082

EXAMPLE 5

2-[9-(1-Azabicyclo[4.3.0]nonyl)]-5-(3-bromo-5-ethylsulphonyl-2-methoxyphenyl)-1H-pyrrole hydrochloride (6,9-syn- and 6,9-anti- isomers)

The title compound was prepared by a method analogous to that used to prepare example 1, but using 2-(3-bromo-5-ethylsulphonyl-2-methoxyphenyl)-1H-pyrrole in place of 2-(3,5-dibromo-2-methoxyphenyl)-1H-pyrrole. As for example 4, it was necessary to perform the Vilsmeier reaction at 100° C.

Faster during pair of diastereoisomers A -Syn (hydrochloride salt)

NMR δ (CDCl$_3$) 1.34 (3H, t, J=7 Hz), 1.46 (1H, m), 1.86 (1H, m), 2.10 (3H, m), 2.32 (2H, m), 2.45 (3H, m), 2.62 (1H, m), 2.98 (1H, m), 3.41 (3H, overlapping m and q, J=7 Hz), 3.85 (3H, s), 4.03 (1H, m), 6.30 (1H, t, J=3 Hz), 6.72 (1H, t, J=3 Hz), 7.97 (1H, d, J=2 Hz), 8.29 (1H, d, J=2 Hz), 11.59 (1H, br.s) and 12.02 (1H, br.s).

Mass spectrum: Found M$^+$ 466.0909; C$_{21}$H$_{27}$BrN$_2$O$_3$S requires 466.0926

Slower eluting pair of diastereoisomers B -Anti (hydrochloride salt)

NMR δ (CDCl$_3$) 1.32 (3H, t, J=7 Hz), 1.50–3.28 (13H, br.m), 3.36 (2H, q, J=7 Hz), 3.85 (3H, s), 4.63 and 5.49 (1H, 2x br.s), 6.31 (1H, br.s), 6.79 (1H, br.s), 7.95 (1H, d, J=2 Hz), 8.26 (1H, br.s), 11.62 (1H, br.s) and 12.15 (1H, br.s).

Mass spectrum: Found M$^+$ 466.0967; C$_{21}$H$_{27}$BrN$_2$O$_3$S requires 466.0926

DATA

The ability of the compounds to bind selectively to human D$_3$ dopamine receptors can be demonstrated by measuring their binding to cloned receptors. The inhibition constants (IC$_{50}$) of test compounds for displacement of [$^{125}$I] iodosulpride binding to D$_3$ dopamine receptors expressed in CHO cells have been determined. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO cell membranes

Cell pellets were gently thawed at room temperature, and resuspended in about 20 volumes of ice-cold 50 mM Tris salts (pH 7.4@37° C.), 20 mm EDTA, 0.2M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4@37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4@37° C.). The final pellet was resuspended in 50 mM Tris salts (pH 7.4@37° C.), and the protein content determined using bovine serum albumin as a standard (Bradford, M. M. (1976) Anal. Biochem. 72, 248–254).

Binding experiments on cloned dopamine receptors

Crude cell membranes were incubated with 0.1 nM [$^{125}$I] iodosulpride (~2000 Ci/mmol; Amersham, U. K.), in a buffer containing 50 mM Tris salts (pH 7.4@37° C.), 120 mM NaCl, 5 mM KCl, 2 mM CaCl$_2$, 1 mM MgCl$_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4@37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models.

Results

The anti- diastereoisomers of Examples 1–5 had IC$_{50}$ values in the range 10.0–50.0 nM, at the D$_3$ receptor.

We claim:

1. A compound of formula (I):

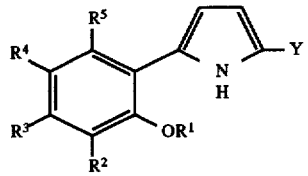

Formula (I)

wherein

R$_1$ represents C$_{1-4}$alkyl; and

R$^2$, R$^3$, R$^4$ and R$^5$ each independently represent hydrogen, halogen, C$_{1-4}$alkyl, C$_{1-4}$alkoxy, C$_{1-4}$alkoxyC$_{1-4}$alkyl, C$_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxyl, hydroxy$C_{1-4}$alkyl, $C_{1-4}$alkylthio, $C_{1-4}$alkanoyl, $C_{1-4}$alkoxycarbonyl, aminosulphonyl, or mono- or di$C_{1-4}$alkylaminosulphonyl; or $R^1$ and $R^2$ together form a linking chain —$(CH_2)_mOp$; (wherein m is 2 to 4 and p is zero or 1) which chain may be optionally substituted by one or two $C_{1-4}$alkyl groups; and Y represents a group of formula:

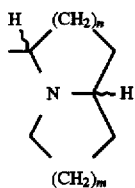

wherein each of n and m independently represent an integer from 1 to 3; and salts thereof.

2. A compound according to claim 1 wherein $R^1$ represents methyl or ethyl, or together with $R^2$ forms a $C_{2-3}$alkylene chain.

3. A compound according to claim 1 wherein at least one of $R^2$ to $R^5$ is hydrogen, and the other substituents are selected from halogen, $C_{1-2}$alkyl, $C_{1-2}$alkoxy, phenylsulphonyl, $C_{1-3}$alkylsulphonyl, $CF_3$ and $CF_3O$.

4. A compound according to claim 1 wherein each of n and m in the group Y independently represent 1 or 2.

5. A compound according to claim 1 selected from:
2-[9-(6,9-anti-(1-azabicyclo[4.3.0]nonyl))]-5-(3,5-dibromo-2-methoxyphenyl)-1H-pyrrole,
2-[2-(2,6-anti-(1-azabicyclo[4.4.0]decyl))]-5-(3,5-dibromo-2-methoxyphenyl)-1H-pyrrole,
2-[9-(6,9-anti-(1-azabicyclo[4.3.0]nonyl))]-5-(5-ethylsulphonyl-2-methoxyphenyl)-1H-pyrrole,
2-[2-(2,6-anti-(1-azabicyclo[4.4.0]decyl))]-5-(3-bromo-5-ethylsulphonyl-2-methoxyphenyl)-1H-pyrrole,
2-[9-(6,9-anti-(1-azabicyclo[4.3.0]nonyl))]-5-(3-bromo-5-ethylsulphonyl-2-methoxyphenyl)-1H-pyrrole,
2-[9-(6,9-syn-(1-azabicyclo[4.3.0]nonyl))]-5-(3,5-dibromo-2-methoxyphenyl)-1H-pyrrole,
2-[2-(2,6-syn-(1-azabicyclo[4.4.0]decyl))]-5-(3,5-dibromo-2-methoxyphenyl)-1H-pyrrole,
2-[9-(6,9-syn-(1-azabicyclo[4.3.0]nonyl))]-5-(5-ethylsulphonyl-2-methoxyphenyl)-1H-pyrrole,
2-[2-(2,6-syn-(1-azabicyclo[4.4.0]decyl))]-5-(3-bromo-5-ethylsulphonyl-2-methoxyphenyl)-1H-pyrrole,
2-[9-(6,9-syn-(1-azabicyclo[4.3.0]nonyl))]-5-(3-bromo-5-ethylsulphonyl-2-methoxyphenyl)-1H-pyrrole, or a salt thereof.

6. A method of treating a condition which requires modulation of a dopamine receptor which comprises administering to a subject in need thereof an effective amount of a compound of formula (I) according to claim 1 or a physiologically acceptable salt thereof.

7. A pharmaceutical composition comprising a compound of formula (I) according to claim 1 or a physiologically acceptable salt thereof and a physiologically acceptable carrier.

* * * * *